United States Patent [19]

Sawaya

[11] Patent Number: 5,519,059
[45] Date of Patent: May 21, 1996

[54] ANTIFUNGAL FORMULATION

[76] Inventor: Assad S. Sawaya, 9 Lyn La., Baiting Hollow, N.Y. 11933

[21] Appl. No.: 291,620

[22] Filed: Aug. 17, 1994

[51] Int. Cl.$^6$ .................................................. A61K 31/16
[52] U.S. Cl. ............................................ 514/599; 514/847
[58] Field of Search ..................................... 514/847, 599

[56] References Cited

U.S. PATENT DOCUMENTS 2,257,106   9/1941   Christiansen ............................... 424/60

OTHER PUBLICATIONS

Pascher, Dermatologic Formulary, 2nd edition, 1957, pp. 28, 29, 31–35 and 42–44.
Merck Index, 9th edition, 1976, p. 1224, #9216.
Glycols, Union Carbide Chemicals Co., 1958, pp. 15 & 16.

*Primary Examiner*—Shelley A. Dodson
*Attorney, Agent, or Firm*—Darby & Darby

[57] ABSTRACT

Disclosed is a topical antifungal formulation including a mixture of isopropyl alcohol, isopropyl myristate and polyethylene glycol or propylene glycol; and a pharmaceutically effective amount of tolnaftate. The formulation provides a solution of tolnaftate which is penetrating, emollient, and non-oily or greasy, non-irritating and rapidly drying. Optionally, aloe vera, vitamin E succinate and witch hazel may be included.

12 Claims, No Drawings

ANTIFUNGAL FORMULATION

FIELD OF THE INVENTION

The present invention relates to an antifungal preparation for topical application. More particularly, the present invention relates to a non-aqueous solution containing the antifungal drug tolnaftate. The solution has emollient properties and is non-oily and non-irritating.

BACKGROUND OF THE INVENTION

The present invention relates to a stable, non-aqueous solution containing tolnaftate for topical application in the treatment of fungal infections.

A fungus is a type of microscopic plant. Fungi include dermatophytes, yeasts and molds characterized by a simple cell structure and the absence of chlorophyll. A dermatophyte is a type of fungus that invades and lives upon the skin or in the hair or nails, resulting in a fungal infection. When the fungal infection involves the scalp, it is known as tinea capitis; when it involves the feet, it is known as tinea pedis (athlete's foot); when it occurs on the body, it is known as tinea corporis; and when it occurs on the groin, it is known as tinea cruris. A fungal infection of the nails in which the invasion is restricted to white patches or pits on the nail surface or the lateral or distal edges of the nail are first involved, followed by establishment of the infection beneath the nail plate, is known as tinea unguium. This type of infection is also known as dermatophytic onychomycosis or ringworm of the nail.

A variety of pharmaceutical compositions are available for the treatment of fungal infections. Such compositions include potassium iodide, Whitfield's ointment (a mixture of benzoic and salicylic acids), undecylenic acid, antibiotics (e.g., nystatin and amphotericin B), griseofulvin and imidazole antifungal agents such as miconazole, and others. Other antifungal agents include haloprogin, tolnaftate, naftifine and ciclopirox.

Tolnaftate is a well-known topical antifungal agent of very low mammalian toxicity. Tolnaftate has an oral $LD_{50}$ in mice and rats of >10 g/kg and >6 g/kg, respectively. Merck Index, 11 Ed., p. 1499.

Tolnaftate has the chemical formula shown below:

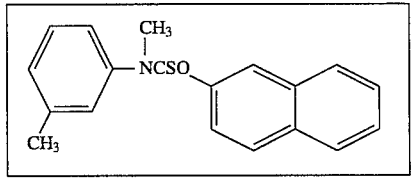

Tolnaftate has a melting point of 110.5° to 111.5° C. and is insoluble in water, sparingly soluble in methanol and ethanol and soluble in chloroform and acetone. Id. The synthesis of tolnaftate is described in U.S. Pat. No. 3,334,126, which is hereby incorporated by reference.

In preparing a formulation for the topical application of tolnaftate for the treatment of fungal infections, it is desirable that the formulation be emollient penetrating, dry rapidly on the skin, be non-irritating to the skin, non-oily or greasy, and not have an objectionable texture or odor. Preferably, the formulation should have a desirable appearance, e.g., a homogeneous, clear solution. In addition, the formulation should be a true solution of tolnaftate, not a suspension. The solution should be stable at a wide range of temperatures to ensure that the tolnaftate does not precipitate from the solution after exposure to the extremes of temperature that the formulation may experience during shipping and storage.

Several commercially available antifungal formulations employ tolnaftate as the active ingredient, generally in an amount of 1% by weight. These formulations include powders, gels, creams, ointments, foams, aerosol powders and topical solutions. Examples of formulations of tolnaftate in solution form identified in the 1993 Physician's Desk Reference for Nonprescription Drugs include: Aftate® aerosol liquid, containing 36% alcohol (Schering-Plough Health-Care, Liberty Corner, New Jersey); Desenex® spray liquid, containing BHT, fragrance, isobutane, polyethylene glycol 400, SD alcohol 40-B (41% w/w) (Fisons Consumer Health, Rochester, N.Y.); Tinactin® 1% solution, containing BHT and PEG. This solution solidifies at low temperatures but liquifies readily on warming, according to the PDR (Schering-Plough HealthCare); and Ting® spray liquid, containing PHT, fragrance, isobutane (propellant), polyethylene glycol 400, SD alcohol 40-B (41% w/w) (Fisons Consumer Health).

Each of these products use high molecular weight PEG, which makes the product extremely oily and hinders skin penetration. In addition, the PEG takes a long time to dry on the skin surface. These products also include alcohol, which improves the drying and skin penetration properties, but does not overcome the disadvantages of the PEG.

Another commercial preparation is Proclearz (distributed by PPR Company, Brooklyn, N.Y. 11232). Proclearz is an antifungal liquid, particularly intended for topical treatment of fungal infections of the nail area. Proclearz includes 1% tolnaftate by weight in a solution containing acetone, water, tocophoryl acetate, propylene glycol and aloe vera gel. However, these solvents are inappropriate for extended use on skin as they may cause irritation and inflammation of the skin.

SUMMARY OF THE INVENTION

The present invention is directed to a topical antifungal formulation including a mixture of isopropyl alcohol, isopropyl myristate and polyethylene glycol or propylene glycol; and a pharmaceutically effective amount of tolnaftate. The formulation provides a solution of tolnaftate which is penetrating, emollient, and non-oily or greasy, non-irritating and rapidly drying. Optionally, aloe vera, vitamin E succinate and witch hazel may be included.

DETAILED DESCRIPTION OF THE INVENTION

The present inventor has discovered that a topical solution containing tolnaftate may be prepared as a clear, stable solution which is penetrating, emollient, and non-oily or greasy, non-irritating and rapidly drying. The solution is prepared using isopropyl alcohol, isopropyl myristate, polyethylene glycol and, optionally, aloe vera and vitamin E succinate.

Tolnaftate is soluble in isopropyl alcohol. Isopropyl alcohol is a good carrier and penetrating agent for delivery of the tolnaftate into the skin. In addition, isopropyl alcohol readily evaporates from the skin and therefore acts to cool the skin, and helps to leave the skin feeling non-greasy after application of the solution. However, isopropyl alcohol can be irritating to the skin and it is therefore desirable to minimize its use in a topical formulation.

Tolnaftate is also soluble in polyethylene glycol 400 ("PEG-400"). PEG-400 is a viscous, slightly hygroscopic liquid having a formula of $H(OCH_2-CH_2)_{8.2-9.1}OH$ and having a molecular weight of about 400. PEG-400 has very low toxicity and is only slightly soluble in aliphatic hydrocarbons. Merck Index, 11 ed., p. 1204. Tolnaftate is also soluble in other molecular weight PEG compounds, including, for example, PEG-200, PEG-600, PEG-1500 and PEG 4000. Tolnaftate is also soluble in propylene glycol.

Isopropyl myristate $(CH_3(CH_2)_{12}COOCH(CH_3)_2)$ is a liquid of low viscosity. It is useful in cosmetic and topical medicinal preparations where good absorption through the skin is desired. Merck Index, 11 ed., p. 821. In addition to being a good skin penetrant, isopropyl myristate is also useful as an emollient. Although tolnaftate is soluble in isopropyl myristate, the proportion of isopropyl myristate in a topical formulation is desirably minimized because when applied to the skin, isopropyl myristate leaves a greasy residue which does not dry easily or quickly.

The present inventor has determined that if the proportions are carefully selected, it is possible to formulate a mixture of PEG-400, isopropyl myristate, isopropyl alcohol and tolnaftate to obtain a pharmaceutically acceptable 1% tolnaftate solution, which is emollient, penetrating, non-greasy and non-irritating. The solution is also stable at a wide range of temperatures, has a low viscosity (less than that of water), and is clear, has no objectionable odor and is colorless. Optionally, small amounts of adjuvants may be included in the formulation. Such adjuvants include Vitamin E succinate, aloe vera gel, fragrance and dyes. Vitamin E and aloe vera serve as skin and nail nutrients.

To prepare a base formulation, studies were conducted to determine the relative miscibility of PEG-400, isopropyl myristate and isopropyl alcohol. Miscibility was determined visually, by observing for layer separation. As set forth in Table 1 below, it was determined that PEG-400 and isopropyl myristate are not miscible with each other when mixed in a ratio of 10 parts PEG-400 to 90 parts isopropyl myristate. These compounds are not miscible at ether ratios either. A mixture of 10 parts PEG-400 and 90 parts isopropyl alcohol formed a solution. Likewise, a mixture of 50 parts isopropyl myristate and 50 parts isopropyl alcohol also formed a solution. When the amount of isopropyl myristate was reduced to 45 parts and the amount of isopropyl alcohol increased to 45 parts, the addition of parts of PEG-400 resulted in a solution.

| Combinations In Parts Per 100 | | | |
|---|---|---|---|
| Polyethylene Glycol 400 | Isopropyl Myristate | Isopropyl Alcohol | Result Of Solubility |
| 10 | 90 | 0 | Not Soluble |
| 10 | 0 | 90 | Soluble |
| 0 | 50 | 50 | Soluble |
| 10 | 45 | 45 | Soluble |

A series of experiments were conducted to determine what proportions if any, of PEG-400, isopropyl myristate, isopropyl alcohol and tolnaftate could be used to obtain a pharmaceutically acceptable 1% tolnaftate solution, which is emollient, penetrating, non-greasy, non-irritating, stable at a wide range of temperatures, has a low viscosity, and is clear, substantially odorless and colorless.

EXAMPLES A THROUGH G

Varying amounts of isopropyl myristate and isopropyl alcohol were mixed to develop a suitable formulation. For these experiments, no PEG-400 was used. Except where otherwise noted, 1.0% by weight of tolnaftate was used, and 0.1% by weight of Vitamin E succinate and 0.1% by weight of Aloe Vera gel were used. All references to percentages are by weight. All weights are in grams. The exact proportion of each component is set forth in Table 2 below.

TABLE 2

| Example | Tolnaftate | Polyethylene Glycol 400 | Isopropyl Myristate | Isopropyl Alcohol | Vitamin E Succinate | Aloe Vera Gel | Witch Hazel | Comments |
|---|---|---|---|---|---|---|---|---|
| A | 1.0% 10.0 g | — | 15.5% 155.0 g | 84.5% 833.0 g | 0.1% 1.0 g | 0.1% 1.0 g | — | Frozen-Thawed Precipitation - crystals occurred |
| B | 1.0% 10.0 g | — | 24.0% 240.0 g | 75.0% 748.0 g | 0.1% 1.0 g | 0.1% 1.0 g | — | Frozen-Thawed Precipitation - crystals occurred |
| C | 1.0% 10.0 g | — | 29.0% 290.0 g | 70.0% 698.0 g | 0.1% 1.0 g | 0.1% 1.0 g | — | Frozen-Thawed Precipitation - crystals occurred |
| D | 1.0% 10.0 g | — | 39.0% 390.0 g | 60.0% 598.0 g | 0.1% 1.0 g | 0.1% 1.0 g | — | Frozen-Thawed Precipitation - crystals occurred |
| E | 1.0% 10.0 g | — | 50.5% 505.0 g | 44.0% 483.0 g | 0.1% 1.0 g | 0.1% 1.0 g | — | Frozen-Thawed Precipitation - crystals occurred |
| F | 1.05% 10.5 g | — | 60.0% 600.0 g | 39.0% 387.5 g | 0.1% 1.0 g | 0.1% 1.0 g | — | Frozen-Thawed Precipitation - crystals occurred |
| G | 1.08% 10.8 g | — | 50.0% 500.0 g | 48.5% 487.2 g | 0.1% 1.0 g | 0.4% 1.0 g | — | Frozen-Thawed Precipitation - crystals occurred |

To prepare the formulation, 1,000 gram batches were prepared by adding a preselected amount of isopropyl myristate (Protameen Chemicals, Totawa, N.J.) to a preselected amount of isopropyl alcohol (Ruger Chemicals, Irvington, N.J.) in a 2,000 cc beaker and the contents mixed using a Lightening mixer (with propeller shaft), at room temperature (22°–25° C.). To this mixture was added 1% by weight of tolnaftate (Napp Chemical, Lodi, N.J.), 0.1% by weight of Aloe Vera gel (in liquid form) (Protameen Chemicals), and 0.1% by weight of Vitamin E succinate (Protameen Chemicals). The mixture was then stirred for an additional 15 minutes.

A 4-ounce sample from the batch was tested for stability of the tolnaftate solution. The sample was placed in a freezer maintained at −4° C. for 16 hours, until the sample was frozen. The sample was then removed from the freezer and allowed to thaw at room temperature for 2 hours. This test is known as the "freeze/thaw" test. For each of Examples A through G, upon thawing a precipitate was detected, indicating that the tolnaftate had come out of solution and that the formulation was unsuitable. As a control, a sample of 100% isopropyl myristate and a sample of 100% isopropyl alcohol were each subjected to the freeze/thaw test. For each control, no precipitation was found upon thawing.

EXAMPLE H THROUGH N

For this series of experiments, witch hazel was included in the formulation. Witch hazel (also known as aqua hamamelis) is an astringent, volatile oil and it was inteded to reduce the harsh effects of the alcohol on the skin. For examples H through M the witch hazel (8.9 or 9.0% by weight) was mixed under gentle heating with 90% by weight of either isopropyl myristate or isopropyl alcohol. The exact proportion of each component is set forth in Table 3 below. In two examples, 0.1% vitamin E succinate was added. In two different examples, 0.1% aloe vera gel was added. For example N, 5.8% witch hazel was mixed with 43.0% isopropyl myristate, 50.0% isopropyl alcohol and 0.1% each of vitamin E succinate and aloe vera gel. 0.1% by weight tolnaftate was added for all examples in this series.

the high alcohol concentration in these samples they "dried out" the skin.

EXAMPLE O

For this example, a mixture of 990 grams of isopropyl myristate and 10 grams of tolnaftate was prepared under gentle heating. This mixture was found to remain as a greasy film on the skin surface, and would not dry fast enough (longer than 30 minutes). The freeze/thaw test was not conducted.

EXAMPLE P

For this example, a mixture of 990 grams of isopropyl alcohol and 10 grams of tolnaftate was prepared under gentle heating. This mixture was unsuitable because the tolnaftate precipated out of solution when the temperature was lowered to room temperature. The freeze/thaw test was not conducted.

EXAMPLE Q, R and S

For these examples PEG-400 was included in the formulation. For Example Q 55.0 grams PEG-400 was mixed with 43.75 grams isopropyl alcohol and 0. 1 grams each of vitamin E succinate and aloe vera gel. 1.05 grams of tolnaftate was added to this mixture. This mixture passed the freeze/thaw test-no precipitation was found upon thawing. However, the resultant mixture was a clear, viscous solution which was oily and did not dry on the skin after 30 minutes of exposure, and was therefore unacceptable for use as a topical solution.

For the next example, (Example R) 43.0 grams isopropyl myristate was mixed with 45.4 grams isopropyl alcohol, 10.5 grams PEG-400, and 0.05 grams each of vitamin E

TABLE 3

| Example | Tolnaftate | Isopropyl Myristate | Isopropyl Alcohol | Vitamin E Succinate | Aloe Vera Gel | Witch Hazel | Comments |
| --- | --- | --- | --- | --- | --- | --- | --- |
| H | 1.0% | — | 90.0% | — | — | 9.0% | Frozen-Thawed - No Precipitation, not emollient - Too harsh on skin |
| I | 1.0% | 90.0% | — | — | — | 9.0% | Frozen-Thawed - Precipitation - crystals occurred |
| J | 1.0% | 90.0% | — | 0.1% | — | 8.9% | Frozen-Thawed - Precipitation - crystals occurred |
| K | 1.0% | — | 90.0% | 0.1% | — | 8.9% | Frozen-Thawed - No Precipitation, not emollient - Too harsh on skin |
| L | 1.0% | — | 90.0% | — | 0.1% | 8.9% | Frozen-Thawed - No Precipitation, not emollient - Too harsh on skin |
| M | 1.0% | 90.0% | — | — | 0.1% | 8.9% | Frozen-Thawed - Precipitation - crystals occurred |
| N | 1.0% | 43.0% | 50.0% | 0.1% | 0.1% | 5.8% | Frozen-Thawed - Precipitation - crystals occurred |

The freeze/thaw test described above was conducted for each of the formulations prepared for this series. The formulations prepared according to Examples I, J, M and N failed the freeze/thaw test-upon thawing, a precipitate formed in the liquid, indicating that the formulation was unstable. Examples H, K and L passed the freeze/thaw test but these formulations were judged to be unsuitable because they did not have sufficient emollient properties and were too harsh on the skin. Emollient properties were measured subjectively by applying a sample to the skin in the wrist area, and allowing it to dry at room temperature. Because of succinate and aloe vera gel. 1.05% of tolnaftate was added after mixing.

This mixture passed the freeze/thaw test-upon thawing the solution remained clear with no visible precipitate. The solution dried quickly (less than 10 minutes) on the skin, and had emollient properties. This formulation represents the preferred embodiment of the present invention.

Finally, for Example S, the same ingredients used in Example R were used, but the proportion of isopropyl myristate was reduced to 37.8 grams, and the amount of isopropyl alcohol was increased to 50.0 grams. PEG-400 was reduced slightly to 10.0 grams. The amounts of Vitamin E succinate and aloe vera gel were increased to 0.1 gram each. 1.0 gram of tolnaftate was added after mixing. This mixture did not pass the freeze/thaw test. This example demonstrates that the proportions of the base ingredients (isopropyl myristate, isopropyl alcohol and PEG-400) are critical to obtaining a tolnaftate solution having the desired properties discussed above. The results of these three experiments are set forth in Table 4 below.

TABLE 4

| Example | Tolnaftate | Polyethylene Glycol 400 | Isopropyl Myristate | Isopropyl Alcohol | Vitamin E Succinate | Aloe Vera Gel | Witch Hazel | Comments |
| --- | --- | --- | --- | --- | --- | --- | --- | --- |
| Q | 1.05% | 55.0% | — | 44.0% | 0.1% | 0.1% | — | Clear Viscous Solution - No Precipitation - Too Oily - Does not dry on skin. Unacceptable |
| R | 1.05% | 10.5% | 43.0% | 45.4% | 0.05% | 0.05% | — | Frozen-Thawed No Precipitation - Clear-Emollient Solution |
| S | 1.0% | 10.0% | 38.0% | 50.0% | 0.1% | 0.1% | — | Frozen-Thawed Precipitation - crystals occurred |

Another series of experiments was conducted wherein the relative amounts of PEG-400, isopropyl myristate and isopropyl alcohol were adjusted. The results of these experiments are set forth below in Table 5.

TABLE 5

| 1% Tolnaftate | PEG 400% | Isopropyl Myristate | Isopropyl Alcohol | Observations |
| --- | --- | --- | --- | --- |
| 1% | -0- | 49.5 | 49.5 | Precipitation |
| 1% | 1 | 48.5 | 49.5 | Precipitation |
| 1% | 2 | 49.5 | 47.5 | Precipitation |
| 1% | 3 | 46 | 50 | Precipitation |
| 1% | 3 | 50 | 46 | Precipitation |
| 1% | 3 | 48 | 48 | Precipitation |
| 1% | 4 | 45 | 50 | Precipitation |
| 1% | 4 | 50 | 45 | Precipitation |
| 1% | 4 | 47 | 48 | Precipitation |
| 1% | 5 | 43 | 51 | Precipitation |
| 1% | 5 | 51 | 43 | Precipitation |
| 1% | 5 | 46 | 48 | Precipitation |
| 1% | 6 | 45 | 48 | Precipitation |
| 1% | 6 | 46.5 | 46.5 | Precipitation |
| 1% | 7 | 48 | 44 | No Precipitation |
| 1% | 7 | 46 | 46 | No Precipitation |
| 1% | 8 | 43 | 48 | No Precipitation |
| 1% | 8 | 48 | 43 | No Precipitation |
| 1% | 8.5 | 42 | 48.5 | No Precipitation |
| 1% | 8.5 | 48.5 | 42 | No Precipitation |
| 1% | 10 | 41 | 48 | No Precipitation |
| 1% | 10 | 48 | 41 | No Precipitation |
| 1% | 11 | 40 | 48 | No Precipitation |
| 1% | 11 | 48 | 40 | No Precipitation |
| 1% | 12 | 40 | 47 | No Precipitation |
| 1% | 12 | 47 | 40 | No Precipitation |
| 1% | 13 | 38 | 48 | No Precipitation |
| 1% | 13 | 48 | 38 | No Precipitation |
| 1% | 13 | 43 | 43 | No Precipitation |
| 1% | 14 | 37 | 48 | Precipitation |
| 1% | 14 | 48 | 37 | Precipitation |
| 1% | 14 | 42 | 43 | No Precipitation |
| 1% | 15 | 36 | 48 | No Precipitation |
| 1% | 15 | 48 | 36 | Precipitation |
| 1% | 16 | 48.5 | 36.5 | Precipitation |
| 1% | 18 | 36 | 45 | Precipitation |
| 1% | 18 | 45 | 36 | Precipitation |
| 1% | 20 | 25 | 54 | No Precipitation |
| 1% | 20 | 34 | 45 | Precipitation |
| 1% | 20 | 40 | 39 | Precipitation |

TABLE 5-continued

| 1% Tolnaftate | PEG 400% | Isopropyl Myristate | Isopropyl Alcohol | Observations |
| --- | --- | --- | --- | --- |
| 1% | 20 | 45 | 34 | Precipitation |
| 1% | 25 | 25 | 49 | Precipitation |
| 1% | 25 | 35 | 39 | Precipitation |
| 1% | 30 | 35 | 34 | Precipitation |

A suitable formulation having the properties identified above can be prepared by mixing between about 35 and about 50% by weight isopropyl myristate, between about 37 and about 50% isopropyl alcohol, and at least about 7% by weight PEG-400, and between about 0.9 and 1.1% by weight of tolnaftate. Optionally, up to about 0.1% by weight of aloe vera gel and up to about 0.1% by weight of vitamin E succinate may be incorporated in the mixture. Witch hazel may also be included. Small amounts of pharmaceutically acceptable fragrances and/or dyes for coloring may be included as well.

The liquid solution of the present invention may be applied to the affected skin using any suitable means, including brush application, pump spray, and aerosol.

What is claimed is:

1. A topical antifungal formulation comprising between about 37 and 50% by weight isopropyl alcohol, between about 35 and 50% by weight isopropyl myristate, between about 7% and 20% by weight polyethylene glycol, and about 1% by weight of tolnaftate.

2. The antifungal formulation of claim 1, wherein said tolnaftate is present in an amount of about 0.9% to 1.1% by weight.

3. The antifungal formulation of claim 1, wherein said mixture includes about 45% by weight isopropyl alcohol, about 43% by weight isopropyl myristate, about 10.5% by weight polyethylene glycol, and about 1.0% by weight tolnaftate.

4. The antifungal formulation of claim 3, further comprising vitamin E succinate.

5. The antifungal formulation of claim 3, further comprising aloe vera.

6. The antifungal formulation of claim 1, further comprising witch hazel.

7. The antifungal formulation of claim 4, wherein said vitamin E succinate is present in an amount of between about 0.05 and 0.1% by weight.

8. The antifungal formulation of claim 5, wherein said aloe vera is present in an amount of between about 0.05 and 0.1% by weight.

9. The antifungal formulation of claim 5, wherein said witch hazel is present in an amount of less than about 10% by weight.

10. The antifungal formulation of claim 1, wherein said polyethylene glycol is selected from the group consisting of PEG-200, PEG-400, PEG-600, PEG-800, PEG-1500, PEG-4000, and mixtures thereof.

11. A topical antifungal formulation, comprising:

a mixture of between about 37% and 50% by weight isopropyl alcohol, between about 35% and 50% by weight isopropyl myristate, between about 7% and 15% by weight polyethylene glycol; and about 1% by weight of tolnaftate.

12. A topical antifungal solution, comprising:

45.4% by weight isopropyl alcohol, 43% by weight isopropyl myristate, 10.5% by weight PEG-400, 0.05% by weight vitamin E succinate, and 0.05% by weight aloe vera; and 1% by weight tolnaftate.

* * * * *